United States Patent
Tucker et al.

(10) Patent No.: US 6,632,199 B1
(45) Date of Patent: Oct. 14, 2003

(54) SYRINGE ASSEMBLY INCLUDING PLASTIC TIP CAP

(75) Inventors: Robyn Laurie Tucker, Basking Ridge, NJ (US); Robert B. Odell, Franklin Lakes, NJ (US); Sandor Szabo, Elmwood Park, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/576,917

(22) Filed: May 23, 2000

(51) Int. Cl.[7] .................................................. A61M 5/32
(52) U.S. Cl. ...................................................... 604/192
(58) Field of Search ................................ 604/192, 193, 604/194; 40/243; 72/105; 70/158; 174/188

(56) References Cited

U.S. PATENT DOCUMENTS

| | | | | |
|---|---|---|---|---|
| 3,578,224 A | * | 5/1971 | Greenhut | 222/526 |
| 3,979,004 A | * | 9/1976 | Bertario | 215/341 |
| 4,237,882 A | * | 12/1980 | Wickham | 604/192 |
| 5,037,389 A | * | 8/1991 | Dooley | 222/526 |
| 5,344,407 A | * | 9/1994 | Ryan | 604/110 |
| 5,533,980 A | * | 7/1996 | Sweeney et al. | 604/110 |
| 5,624,402 A | * | 4/1997 | Imbert | 604/111 |
| 5,658,254 A | * | 8/1997 | Reichenbach et al. | 604/110 |
| 5,820,603 A | * | 10/1998 | Tucker et al. | 604/111 |
| 5,857,580 A | * | 1/1999 | Iidaka | 215/250 |
| 6,065,645 A | * | 5/2000 | Sawhney et al. | 222/137 |
| 6,170,705 B1 | * | 1/2001 | Schneider et al. | 222/107 |
| 6,241,705 B1 | * | 6/2001 | Ko-Wen | 604/73 |

* cited by examiner

*Primary Examiner*—Daniel Robinson
(74) *Attorney, Agent, or Firm*—Jeanne P. Lukasavag

(57) ABSTRACT

A syringe assembly includes a plastic cap (20) that has an end wall (22) and a side wall (24). The end wall (22) preferably includes a plug portion (64) that extends away from an inner surface (62) of the end wall (22). The side wall (24) includes an inner surface (28) that has an engaging portion that sealingly engages a corresponding surface on a syringe. The engaging portion preferably includes two generally annular ribs (34) and (36). An interference fit is provided between the engaging portion and a corresponding surface on the syringe to maintain a sterile seal where the engaging portion contacts the syringe. The plug portion is received within an opening in the syringe and maintains a sterile seal at that point while simultaneously maintaining any medicament within the syringe.

12 Claims, 12 Drawing Sheets

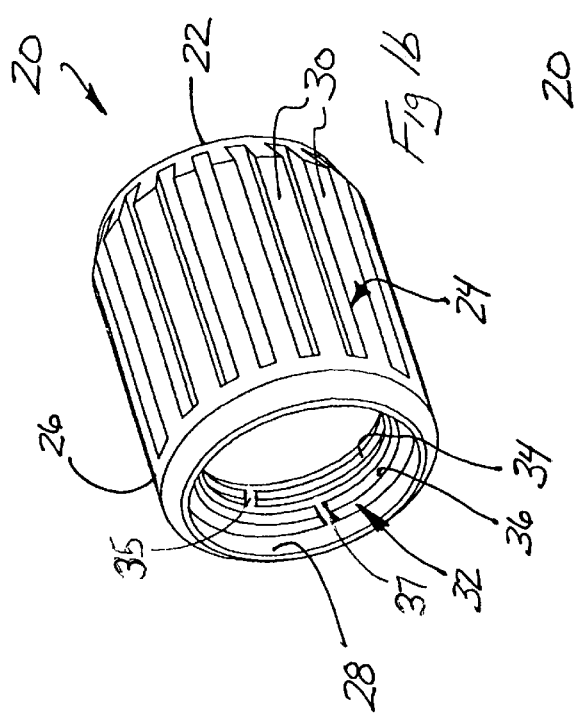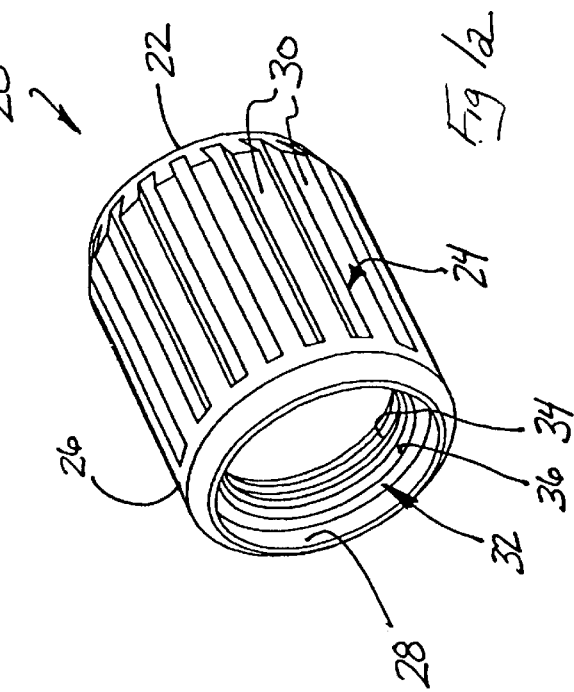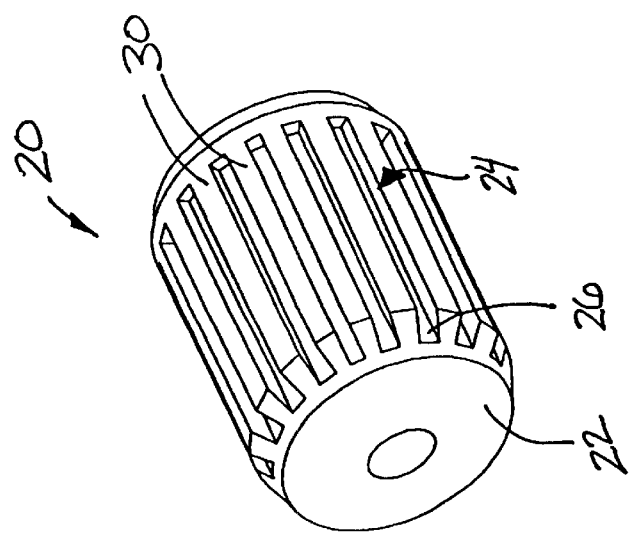
FIG-1

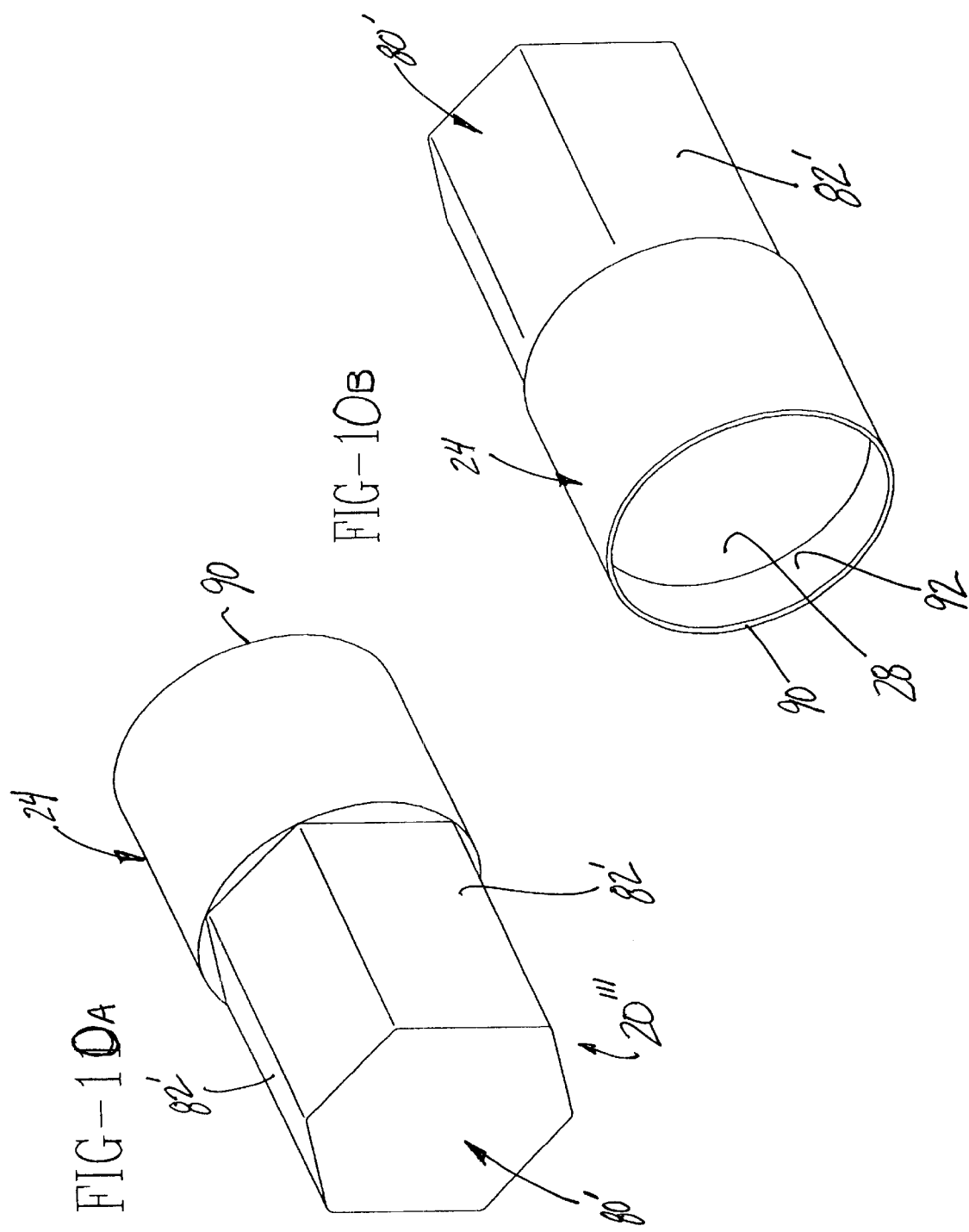

SYRINGE ASSEMBLY INCLUDING PLASTIC TIP CAP

BACKGROUND OF THE INVENTION

This invention generally relates to syringe assemblies and, more particularly, to an assembly including a plastic tip cap for sealing off the end of a prefillable syringe.

A variety of syringe assemblies are commercially available. Some syringe assemblies are prefilled with a medicament, while others are supplied empty and are later filled by a medical professional, for example. In either situation, it is typically imperative to maintain sterility of the syringe assembly during shipment, handling and up to the point of actual use. One example arrangement for supplying prefilled syringes includes a rubber cap portion that is received over the end of a glass syringe body. The rubber cap portion is intended to seal the syringe body closed to maintain the prefilled medicament within the syringe until it is desirable to dispense the medicament during an injection. While such rubber cap portions have proven useful, they are not without shortcomings and drawbacks.

One shortcoming of rubber cap portions is that rubber material is relatively difficult to manufacture within tight tolerances. In situations where very specific dimensional constraints exist, rubber cap portions often do not meet the specific requirements. Another problem associated with rubber cap portions is that rubber material is relatively expensive to utilize during a manufacturing process. Further, rubber material may present the possibility of interacting with a medicament stored within a prefilled syringe when the medicament comes in contact with the rubber material.

Therefore, it is desirable to provide an improved syringe assembly having cap portion that avoids the shortcomings and drawbacks of the rubber cap portions described above. This invention meets that need.

SUMMARY OF THE INVENTION

In general terms, this invention is a syringe assembly including a plastic cap that closes off one end of a syringe. The plastic cap seals the syringe closed to maintain a prefilled medicament within the syringe while simultaneously maintaining the sterility of the appropriate portions of the syringe.

A plastic cap designed according to this invention includes an end wall having an outer surface and an inner surface with a plug portion extending away from the inner surface. A continuous side wall extends from the end wall in the same direction as the plug portion. The side wall has an outer surface and an inner surface with at least one engaging portion on the inner surface. The engaging portion is biased into sealing engagement with a corresponding portion of a syringe and the plug portion is received into an opening on the syringe when the cap is received on the end of the syringe.

In the preferred embodiment, the engaging portion includes at least one generally annular rib on the inner surface of the side wall. The plug portion maintains the sterility of the opening in the end of the syringe, while the engaging portion maintains the sterility of a coupling portion near the end of the syringe, which preferably is designed to accommodate a conventional hypodermic needle.

The plastic cap of this invention is especially useful with syringe bodies that are made from plastic materials. The engaging portion of the cap preferably has a dimension that cooperates with a corresponding surface on the syringe so that an interference fit is established when the cap is placed on the end of the syringe.

The various features and advantages of this invention will become apparent to those skilled in the art from the following detailed description of the currently preferred embodiments. The drawings that accompany the detailed description can be briefly described as follows.

BRIEF DESCRIPTION OF THE DRAWINGS

FIGS. 1 and 1a are perspective illustrations of a cap designed according to this invention.

FIG. 1b shows an alternative arrangement of portions of the embodiment of FIGS. 1 and 1a.

FIG. 2 is a perspective illustration of a syringe assembly including the embodiment of FIGS. 1 and 1a.

FIG. 4 is a cross-sectional illustration of the embodiment of FIGS. 1 and 1a.

FIG. 5 is an elevational view of the embodiment of FIGS. 1 and 1a.

FIGS. 10a and 10b are perspective illustrations of another example embodiment of a cap designed according to this invention.

DETAILED DESCRIPTION OF THE PREFERRED EMBODIMENTS

Figure 2:
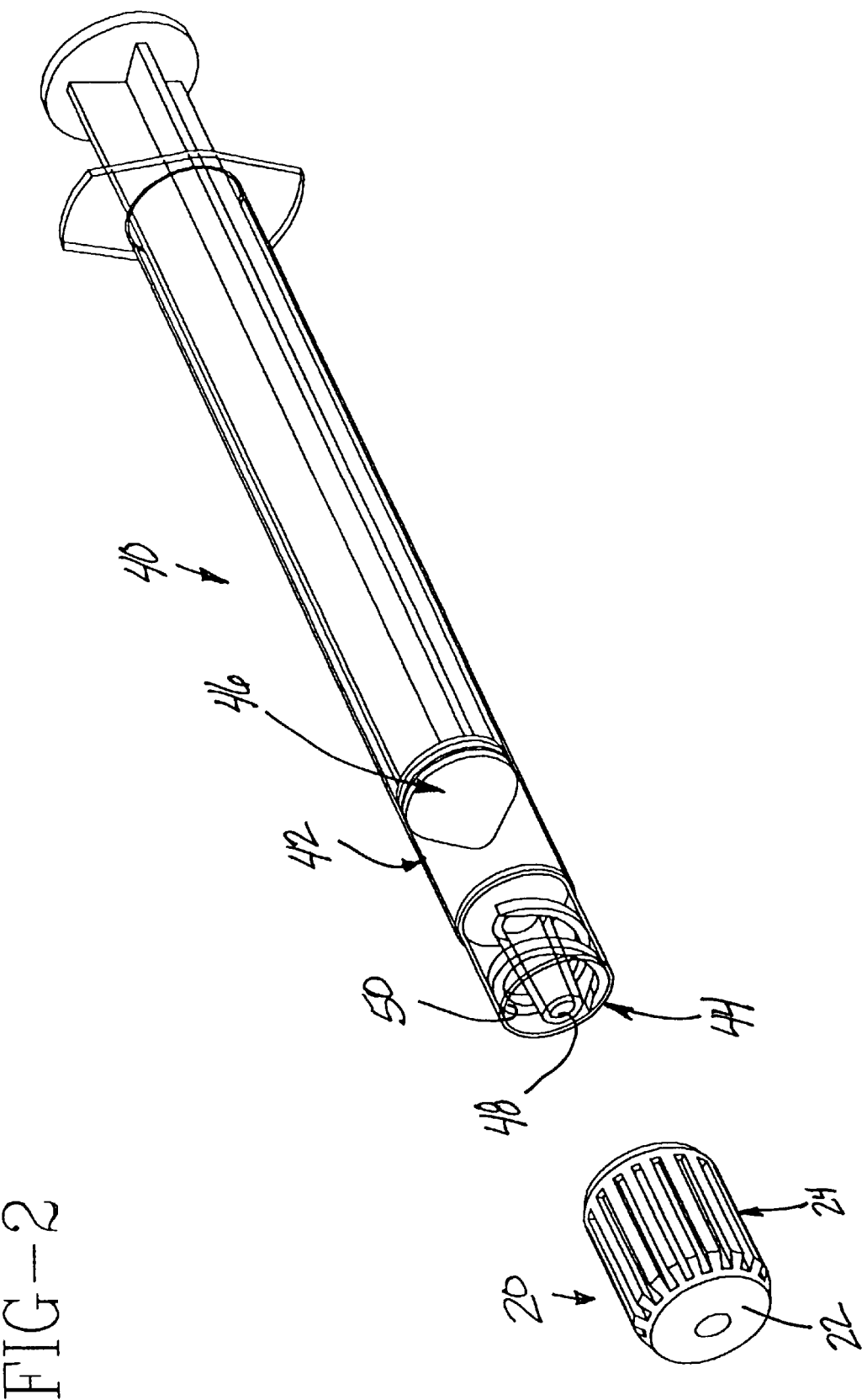

FIGS. 1 and 1a show a cap 20 in perspective from two different views. The cap 20 includes an end wall 22 and a side wall 24. In this embodiment, the end wall 22 and the side wall 24 preferably are continuous and made from a single piece of plastic material. A variety of plastic molding techniques such as injection molding can be used to form the cap 20.

The side wall 24 preferably is generally cylindrical to accommodate conventional syringe designs. The side wall 24 has an outer surface 26 and an inner surface 28. The outer surface 26 preferably includes a plurality of ridges or splines 30 that extend axially along the outer surface 26. The ridges 30 facilitate handling the cap 20 when placing it onto a syringe or removing it from a syringe, respectively.

The cap 20 preferably is used with a plastic syringe body 40 as shown in FIG. 2. The syringe 40 includes a barrel portion 42 that is adapted to contain a medicament, which can be prefilled by a pharmaceutical company before shipment to an end user. One end 44 of the syringe 40 is adapted to be connected with a conventional hypodermic needle (not shown) to make an injection. A conventional plunger arrangement 46 is provided for expelling any medicament from the barrel portion 42 through an opening 48 in the end 44 of the syringe 40 when an injection is desired. The illustrated syringe 40 includes a Luer collar 50 for connecting the syringe 40 with a conventional hypodermic needle having a Luer fit attachment as is known in the art.

The syringe 40 and the cap 20 preferably are made from plastic materials. The materials selected for the syringe 40 and the cap 20 can be the same such as polypropylene or different such as using polypropylene for the syringe 40 and polyethylene for the cap 20. The cap can also be made from a combination of plastic, rubber or thermoplastic elastomer materials, any of which is referred to generically as a plastic in this description.

Figure 3:
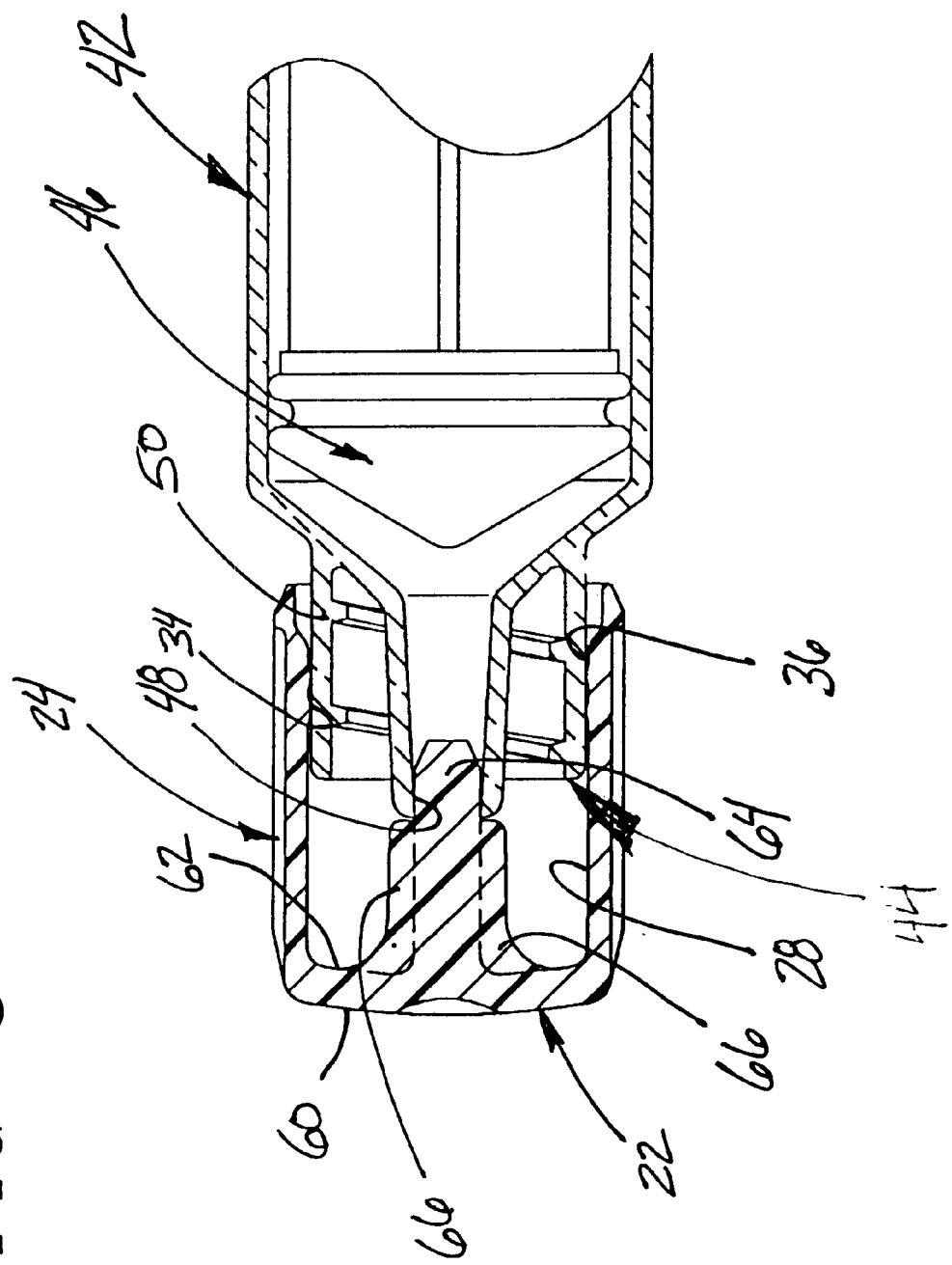
FIG. 3 is a partial, cross-sectional view of the embodiment of FIG. 2 in an assembled condition.
Figure 4:
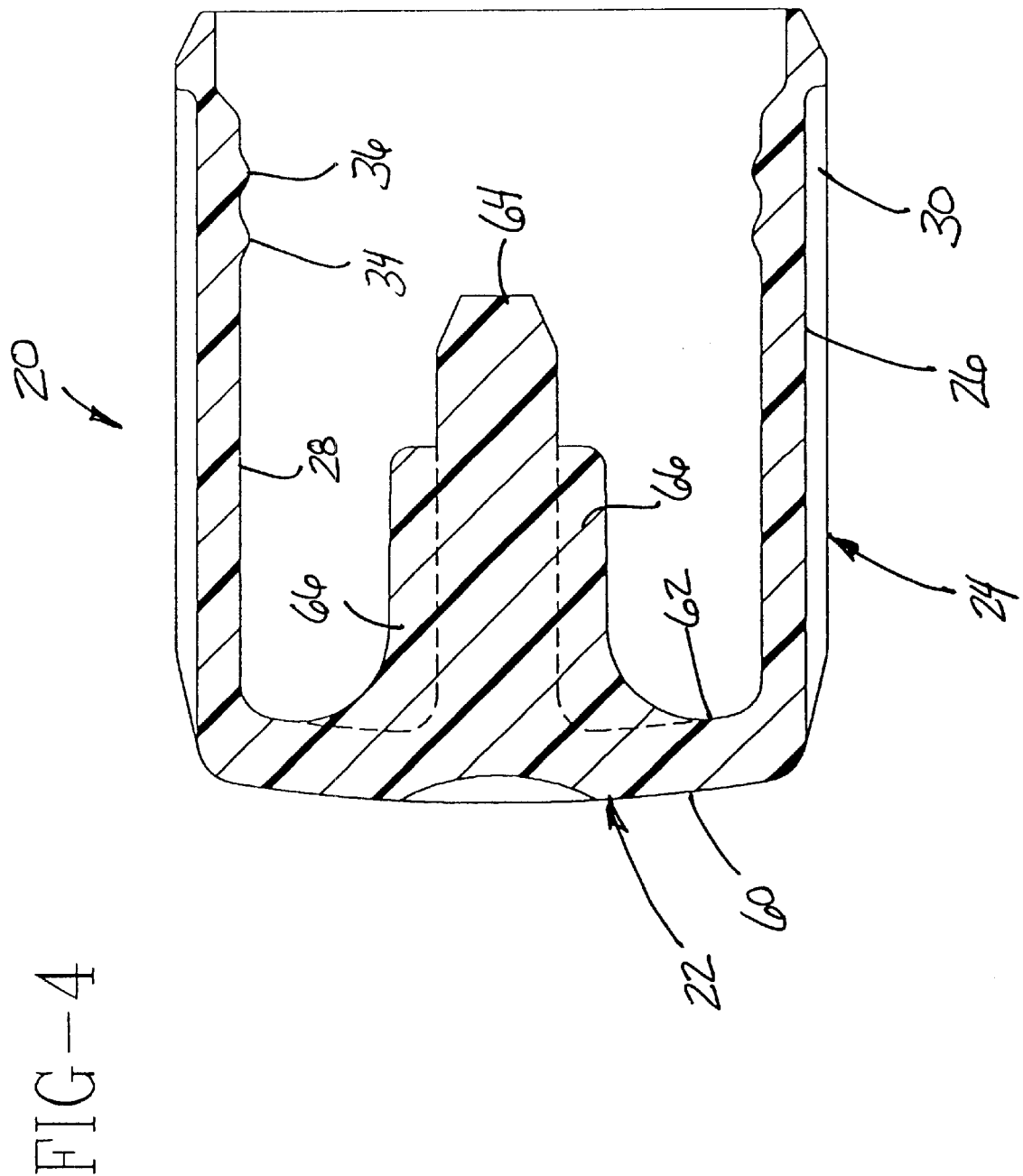
Figure 5:
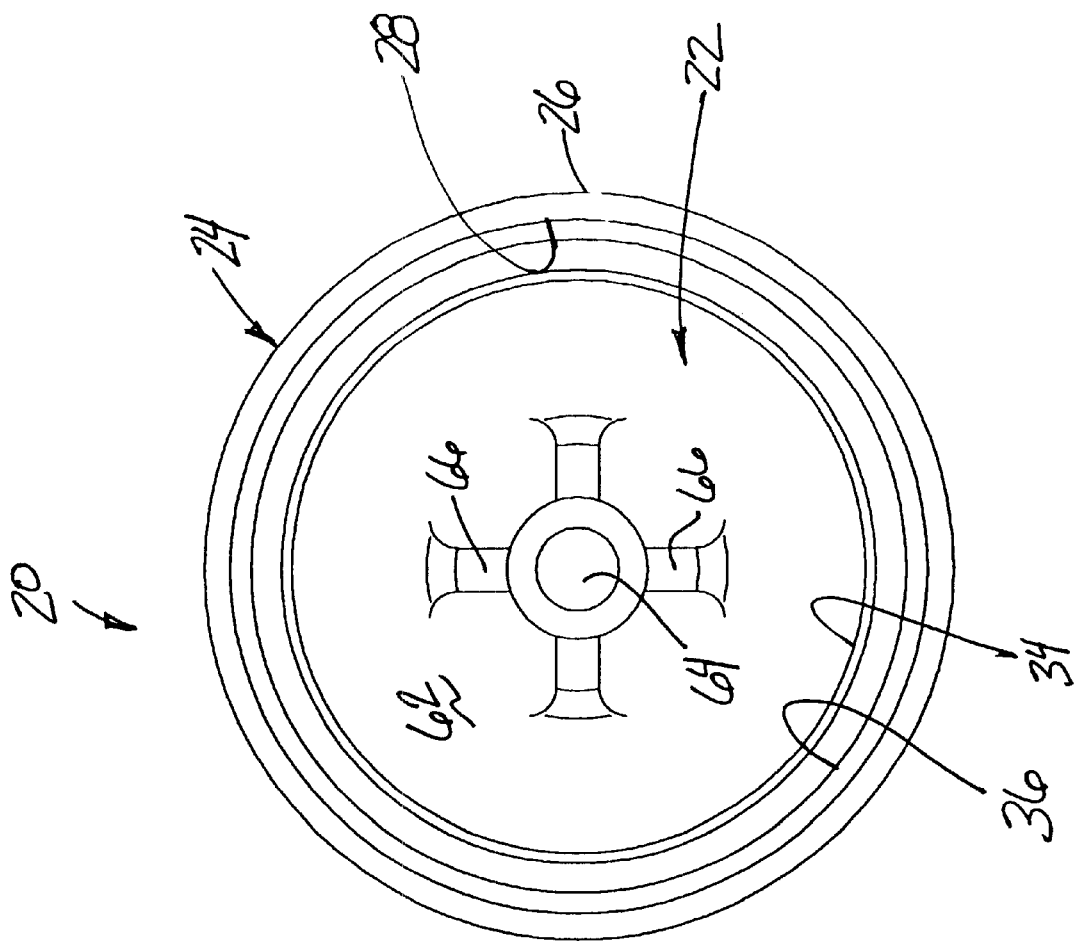

As can be best appreciated from FIGS. 3, 4 and 5, the cap 20 is received onto the end 44 of the syringe 40 to provide a sterility seal and a seal that maintains any medicament within the barrel portion 42. The cap 20 preferably provides a seal at two different locations on the end of the syringe 44.

The end wall 22 has an outer surface 60 and an inner surface 62. A sealing projection or plug portion 64 extends away from the inner surface 62. A plurality of ribs 66 preferably extend along a portion of the length of the plug portion 64 to provide stability and structural integrity. As can be seen in FIG. 3, the end of the plug portion 64 is received within the opening 48 on the syringe 40 when the cap 20 is secured in place. The plug portion 64 provides a sterility seal at the opening 48. Additionally, the plug portion 64 operates to maintain any medicament within the barrel portion 44 of the syringe 40.

A second seal is provided by an engaging portion on the inner surface 28 of the side wall 24. In this embodiment, the engaging portion includes two generally annular ribs 34 and 36. The dimensions of the Luer collar 50 and the inner diameters defined by the ribs 34 and 36 preferably provides a tight, sealing, interference fit between the syringe 40 and the cap 20. The engaging portion of the cap 20 ensures that the end 44 of the syringe 40 remains sterile during shipment and handling.

Providing two ribs 34 and 36 is preferred to provide a better quality seal and ensure that sterility is maintained even if one of the ribs were to have a defect or be damaged during handling or assembly. The cap 20 provides a seal at two different points (i.e., around the outside of the Luer collar 50 and inside of the opening 48) to maintain sterility of the syringe assembly.

In the preferred embodiment, the inside diameters defined by the ribs 34 and 36 preferably are slightly different. It is most preferred to have an inside diameter defined by the rib 34 to be slightly smaller than the inside diameter defined by the rib 36. This can be accomplished by having the rib 34 have a larger cross-section compared to the rib 36. Alternatively, a gradual outward slope on the inner surface 28 may be provided so that the rib 36 does not protrude inward as far as the rib 34. Alternatively, the ribs 34 and 36 can have equal dimensions.

FIG. 1b shows an alternative arrangement where the ribs 34 and 36 include a non-continuous perimeter. Rib 34 includes a break at 35 and rib 36 includes a break at 37. The breaks 35 and 37 most preferably are not aligned with each other. In one example, the breaks 35 and 37 are spaced apart by 180 degrees.

The breaks 35 and 37 provide a tortuous path along which a sterilizing fluid such as steam or ethylene oxide may travel to sterilize the end 44 of the syringe after the cap 20 is in place on the syringe. A tortuous path or labyrinth seal arrangement of this type allows sterilization but will not permit infiltration of undesired bacteria or microbes so that sterilization is maintained. The ability to provide such an arrangement was not possible with conventional tip caps because proper tolerances could not be maintained during the manufacturing process.

The components chosen for the syringe 40 and the cap 20 will have an impact on the tightness of the interference fit between the components. The interference fit preferably is relatively high to ensure a reliable seal during the entire storage life of the product. Therefore, removing the cap 20 from the syringe 40 should be relatively difficult. The ridges 30 on the outer surface 26 of the side wall 24 facilitate removing the cap 20 from the syringe when necessary. Depending on the material selected for the tip 20 and the syringe 40, the difficulty of removal can be controlled. Given this description, those skilled in the art will be able to choose from among various materials to achieve the desired results for particular situations.

The plastic cap 20 provides advantages and improvements compared to previous caps, which were typically made of rubber materials. Plastic provides economic advantages because it can be molded less expensively and more cleanly than rubber materials. Additionally, the plastic material for the cap 20 can be made relatively transparent to allow improved inspection of the integrity of the seal provided by the engaging portion and the plug portion of the cap. Moreover, dimensional control to meet specific tolerance requirements is possible with plastic material that far exceeds the performance of rubber materials.

Figure 6:
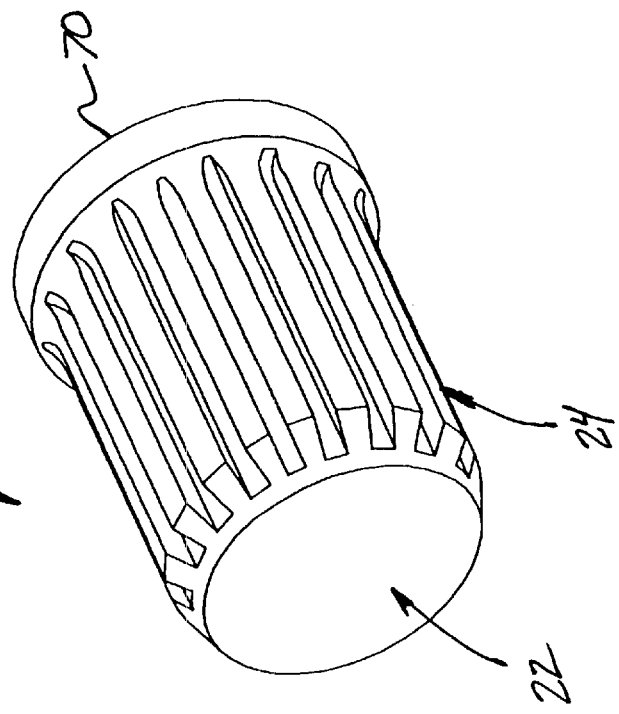
FIGS. 6 and 6a are perspective illustrations of an alternative embodiment of a cap designed according to this invention.
Figure 6A:
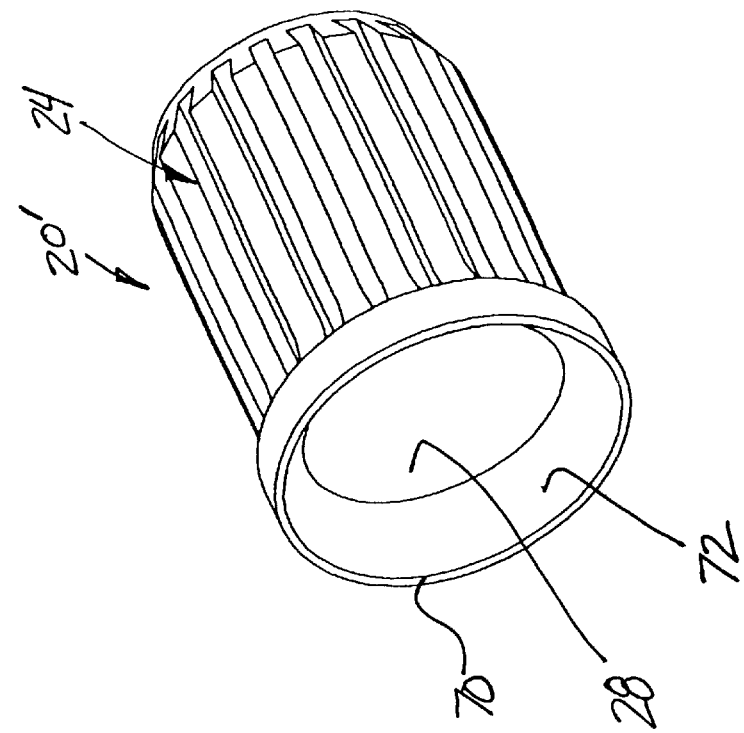
Figure 7:
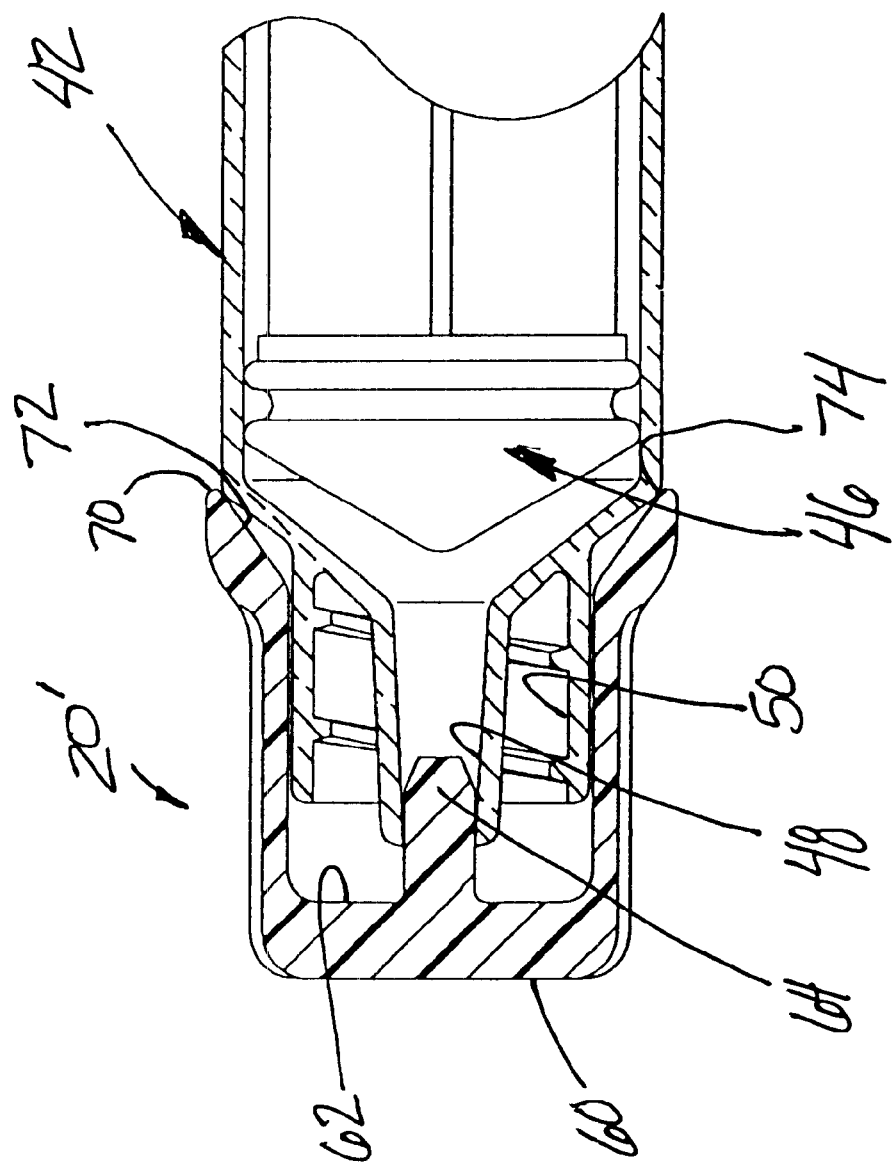
FIG. 7 is a partial, cross-sectional illustration of the embodiment of FIGS. 6 and 6a shown received on the end of a syringe.

FIGS. 6, 6a and 7 illustrate an alternative embodiment of a cap designed according to this invention. The cap 20' includes a terminal edge 70 that is distal from the end wall 22. The engaging portion on the cap 20' is a sloped surface 72 immediately adjacent the terminal edge 70. The sloped surface 72 preferably engages an end surface 74 on the barrel portion 42 of the syringe 40. This arrangement provides a seal at the interaction between the engaging portion surface 72 and the end surface 74 of the barrel 42 so that the entire Luer collar 50 is kept within a sterile environment during shipment and handling. This style of cap 20' is especially useful when a syringe has a Luer collar 50 with a smaller outside dimension than the outside dimension of the barrel 42 as can be appreciated from FIG. 7.

Figure 8:
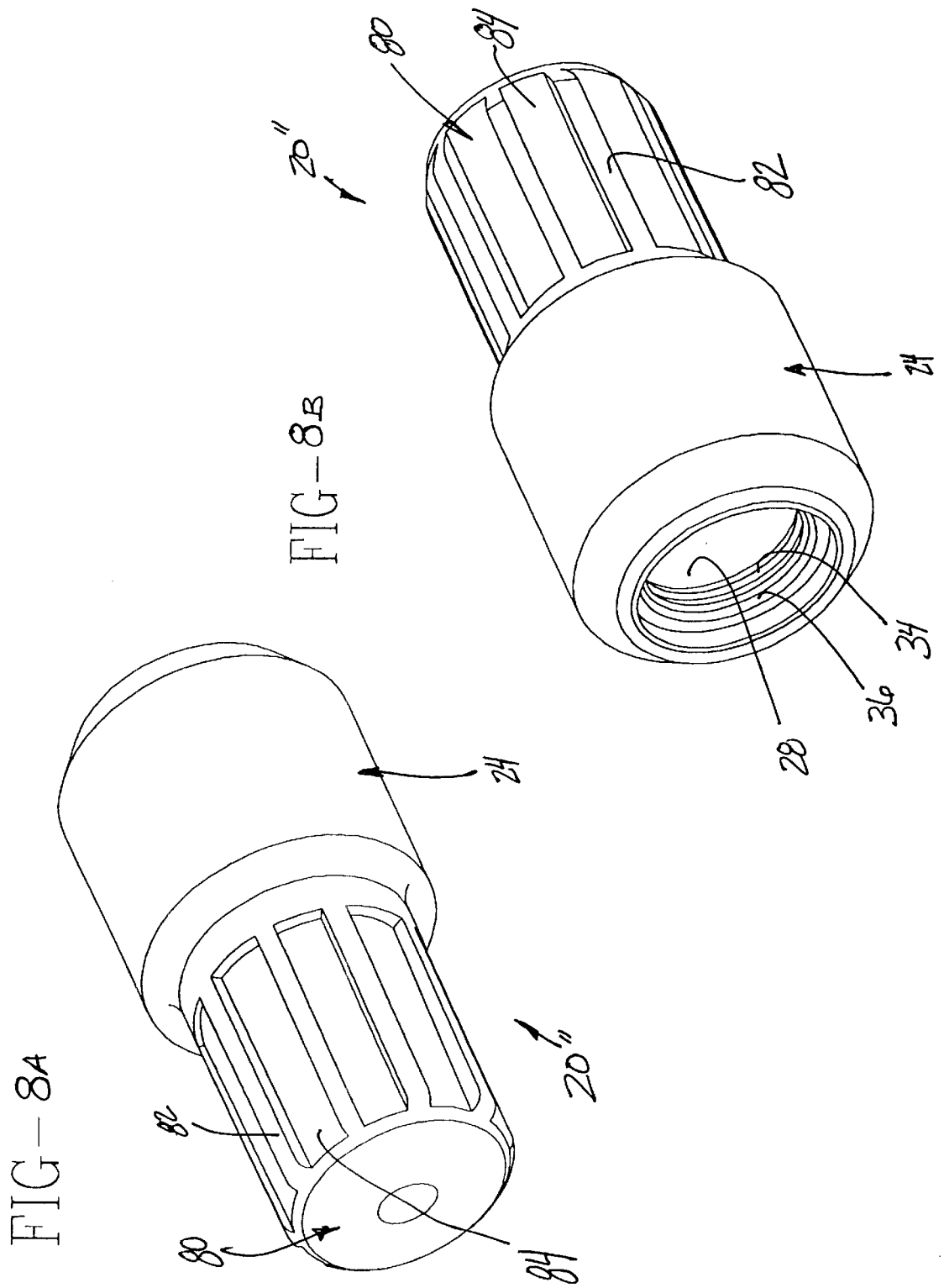
FIGS. 8a and 8b are perspective illustrations of another example embodiment of a cap designed according to this invention.
Figure 9:
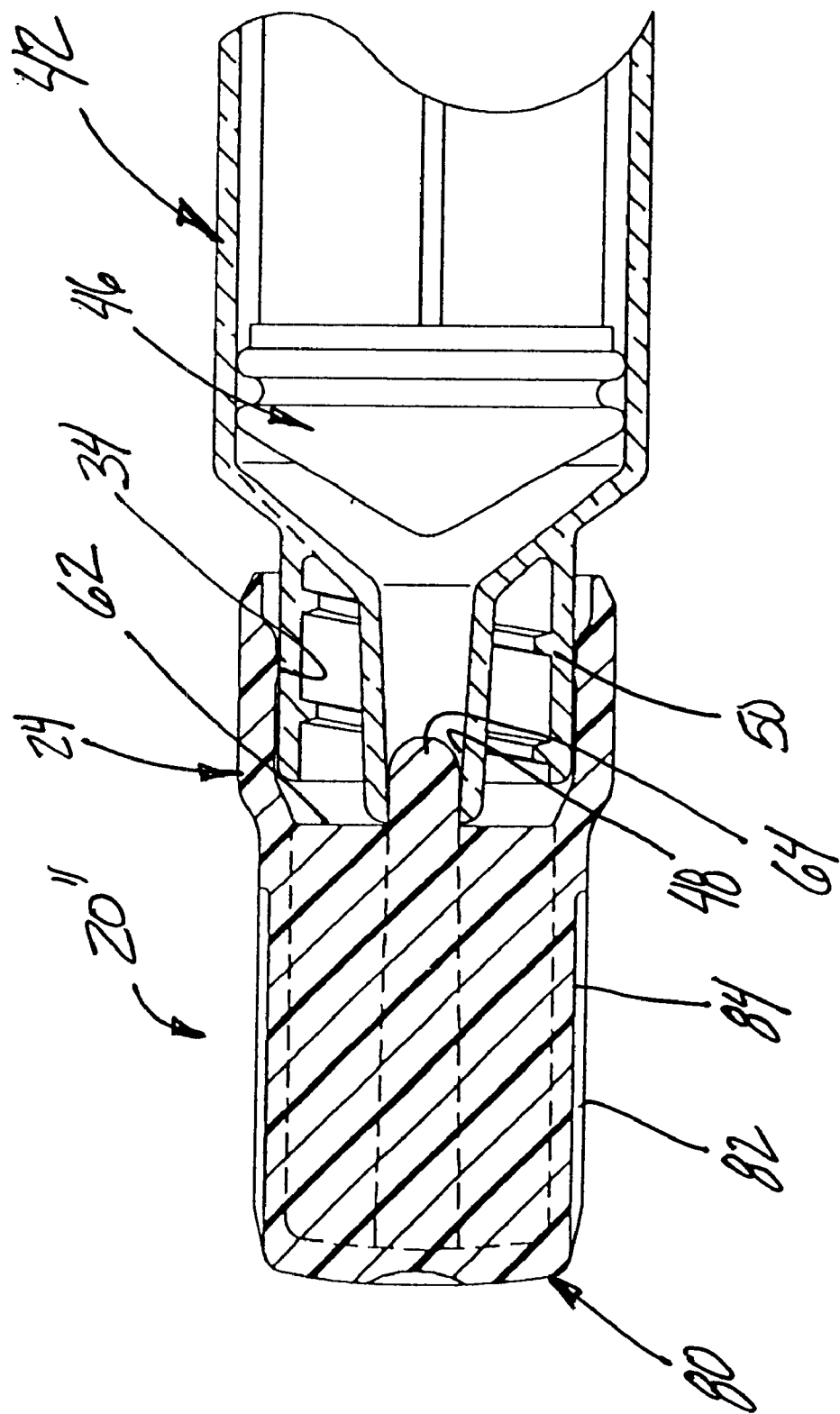
FIG. 9 is a partial, cross-sectional view of the embodiment of FIGS. 8a and 8b shown received on the end of a syringe.
Figure 12:
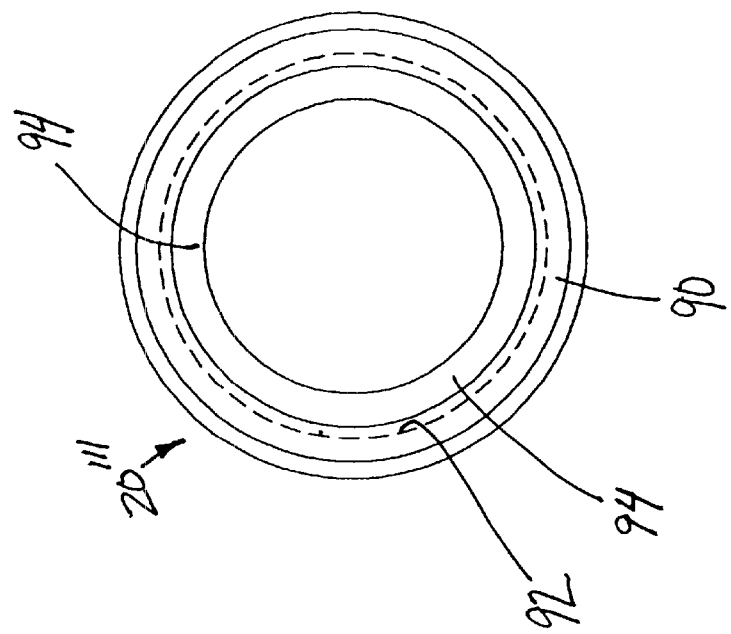
FIG. 12 is an elevational view of the embodiment of FIGS. 10a and 10b.
Figure 11:
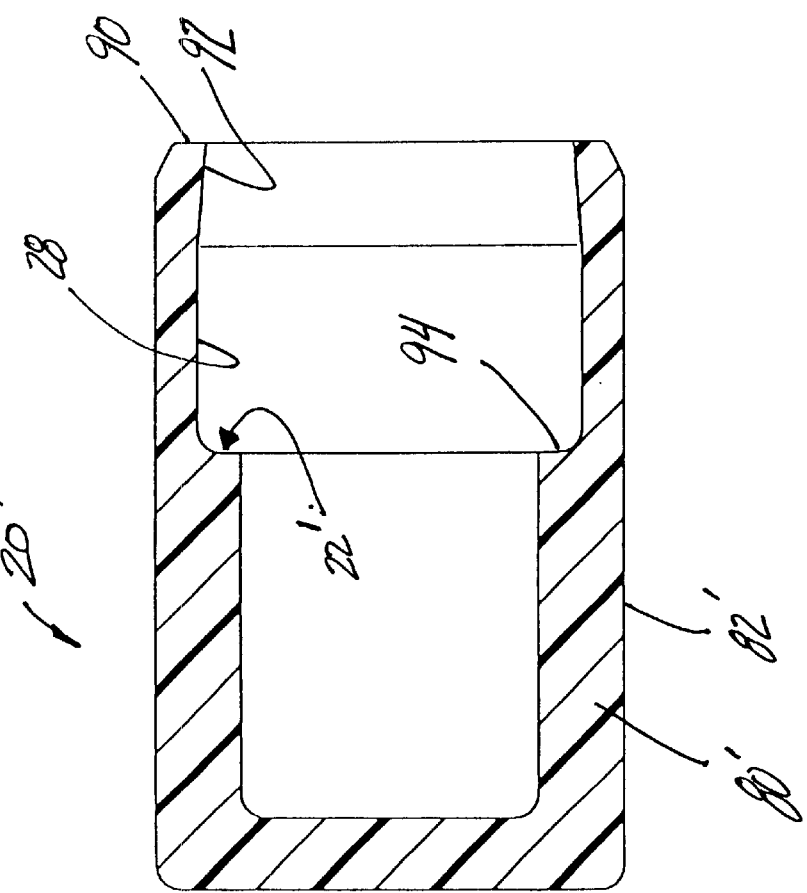
FIG. 11 is a cross-sectional illustration of the embodiment of FIGS. 10a and 10b.
Figure 13:
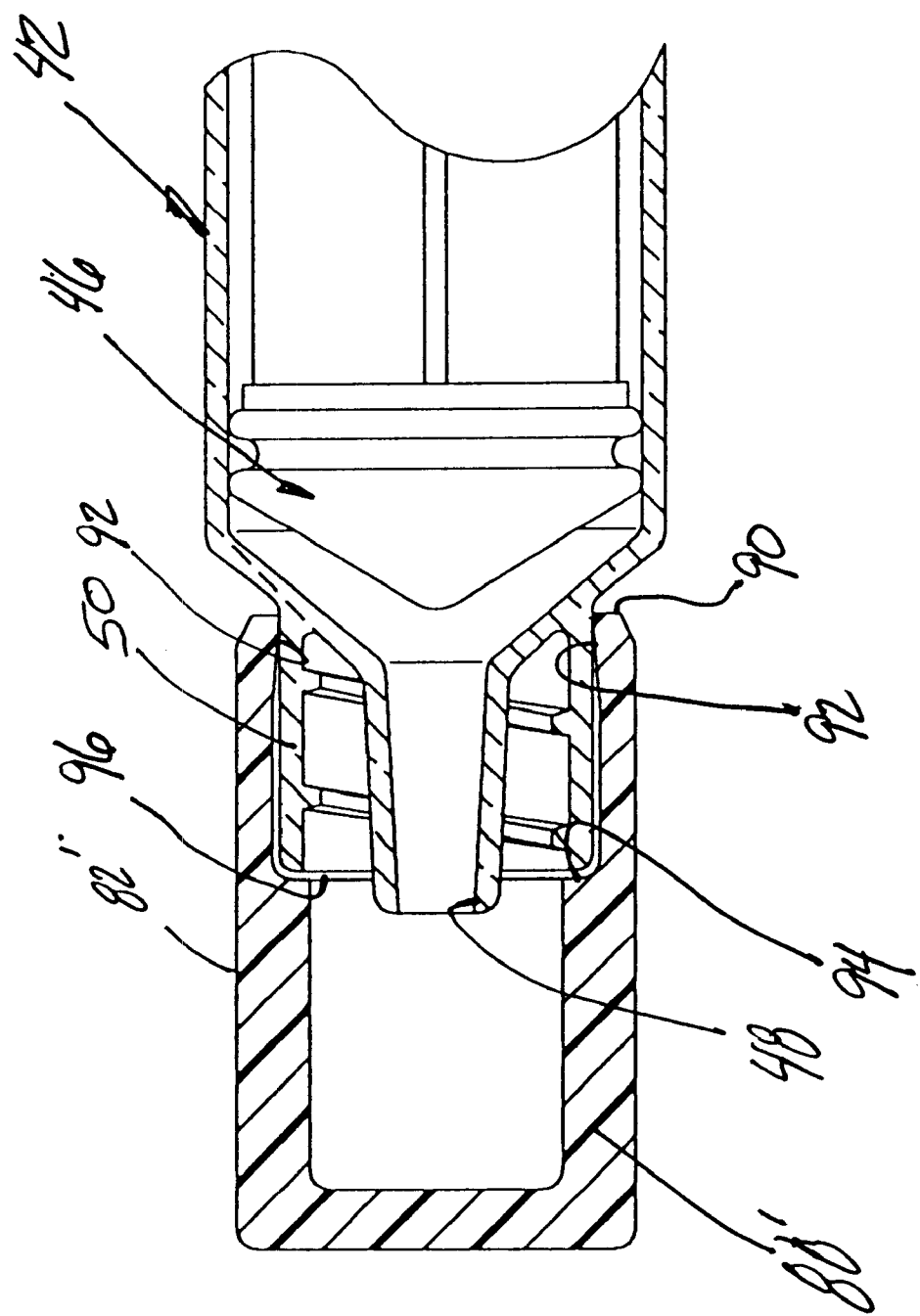
FIG. 13 is a partial, cross-sectional view of the embodiment of FIGS. 10a and 10b shown received on the end of a syringe.

FIGS. 8a, 8b and 9 illustrate another example embodiment of a cap designed according to this invention. The cap 20" includes an extension 80 extending away from the end wall in a direction opposite from the side wall 24. The extension 80 preferably includes a plurality of ridges or splines 82 on an outer surface 84 of the extension. The ridges 82 facilitate handling the cap 20". The additional surface area provided by the extension 80 provides an enlarged cap 20" compared to the examples described above. The example illustrated in FIGS. 8a and 8b includes an engaging portion that has two ribs 34 and 36 as described above.

FIGS. 10a through 13 illustrate yet another example of a cap designed according to this invention. The cap 20''' includes an extension 80' having a plurality of exterior surfaces 82' that are arranged in a generally hexagonal configuration. The extension 80' facilitates handling the cap 20''' for placing it onto or removing it from a syringe.

The cap 20''' includes a terminal edge 90 that is distal from the end wall 22'. In this embodiment, the engaging portion is a generally inward sloping surface 92 that is immediately adjacent the terminal edge 90. In this embodiment, the end wall 22' is preferably not continuous. Instead, the end wall 22' provides a shelf portion 94 that sealingly engages an edge 96 on the Luer collar 50 to provide a seal that surrounds, but does not contact the opening 48 of the syringe 40. An interference fit between the sloping surface 92 and the Luer collar 50 provides the seal at the second point, preferably near the edge of the Luer collar 50.

The preceding description provides details regarding several examples of caps designed according to this invention. Variations and modifications may become apparent to those skilled in the art that do not necessarily depart from the basis of this invention. The scope of legal protection given to this invention can only be determined by studying the following claims.

What is claimed is:

1. A cap for closing off an end of a syringe, comprising:
   an end wall having an outer surface and an inner surface with a plug portion extending away from the inner surface;
   a continuous side wall extending from the end wall in the same direction as the plug portion, the side wall having an outer surface and an inner surface with at least one contact portion on the inner surface;
   wherein the end wall and side wall are formed as a single plastic piece and the engaging portion is biased into sealing engagement with an outside surface of a collar portion of a syringe body and the plug portion is received into an opening on the syringe when the cap is received onto a syringe.

2. The cap of claim 1, wherein the engaging portion includes two ribs on the inner surface of the side wall.

3. The cap of claim 2, wherein the ribs are generally annular.

4. The cap of claim 2, wherein a first one of the ribs defines a first inner diameter and a second one of the ribs defines a second inner diameter that is greater than the first inner diameter.

5. The cap of claim 4, wherein the side wall includes a terminal edge distal from the end wall and the second one of the ribs is positioned closer to the terminal edge than the first one of the ribs.

6. The cap of claim 1, wherein a portion of the side wall inner surface defines a first inner dimension and the engaging portion defines a second inner dimension that is smaller than the first inner dimension.

7. The cap of claim 1, wherein a portion of the side wall inner surface defines a first inner dimension and the engaging portion defines a second inner dimension that is greater than the first inner dimension.

8. The cap of claim 7, wherein the side wall includes a terminal edge distal from the end wall and the engaging portion is located adjacent the terminal edge.

9. The cap of claim 1, wherein the side wall outer surface includes a plurality of ridges that facilitate handling the cap when placing the cap onto a syringe or removing the cap from a syringe.

10. The cap of claim 1, including an extension extending away from the end wall in a direction opposite from the side wall and wherein the extension includes a plurality of exterior surfaces that facilitate handling the cap when placing the cap onto a syringe or removing the cap from a syringe.

11. The cap of claim 1, including a plurality of ribs extending away from the end wall inner surface and supporting the plug portion along at least a portion of a length of the plug portion.

12. The cap of claim 1, including at least two ribs on the inner surface of the side wall and wherein each rib includes a non-continuous perimeter with at least one break portion, the break portions being at different locations on the ribs, respectively.

* * * * *